(12) United States Patent
Yu et al.

(10) Patent No.: US 10,914,705 B2
(45) Date of Patent: Feb. 9, 2021

(54) ELECTROCHEMICAL SENSOR

(71) Applicant: Honeywell International Inc., Morris Plains, NJ (US)

(72) Inventors: Yuzhong Yu, Shanghai (CN); Na Wei, Shanghai (CN); Ling Liu, Shanghai (CN)

(73) Assignee: Honeywell International Inc., Morris Plains, NJ (US)

( * ) Notice: Subject to any disclaimer, the term of this patent is extended or adjusted under 35 U.S.C. 154(b) by 179 days.

(21) Appl. No.: 16/069,271

(22) PCT Filed: Jan. 12, 2016

(86) PCT No.: PCT/US2016/012961
§ 371 (c)(1),
(2) Date: Jul. 11, 2018

(87) PCT Pub. No.: WO2017/123205
PCT Pub. Date: Jul. 20, 2017

(65) Prior Publication Data
US 2019/0025243 A1 Jan. 24, 2019

(51) Int. Cl.
G01N 27/404 (2006.01)
G01N 33/00 (2006.01)

(52) U.S. Cl.
CPC ..... *G01N 27/4045* (2013.01); *G01N 33/0044* (2013.01)

(58) Field of Classification Search
CPC .................. G01N 27/4045; G01N 33/0044
See application file for complete search history.

(56) References Cited

U.S. PATENT DOCUMENTS

| 4,042,464 | A  | 8/1977  | Blurton et al.          |
|-----------|----|---------|--------------------------|
| 4,591,414 | A  | 5/1986  | Zaromb et al.           |
| 4,636,294 | A  | 1/1987  | Novack et al.           |
| 5,173,166 | A  | 12/1992 | Tomantschger et al.     |
| 7,378,008 | B2 | 5/2008  | Inoue et al.            |
| 8,840,775 | B2 * | 9/2014 | Chen ............ G01N 27/4045 |
|           |    |         | 205/786.5               |
| 2009/0120794 | A1 | 5/2009 | Jones                |
| 2011/0183232 | A1 | 7/2011 | Tsou et al.          |

(Continued)

FOREIGN PATENT DOCUMENTS

| CN | 101151526 A | 3/2008 |
| CN | 101325259 B | 7/2010 |

(Continued)

OTHER PUBLICATIONS

EPO computer-generated English language translation of Wang et al. CN102621205A, patent published Aug. 1, 2012 (Year: 2012).*

(Continued)

*Primary Examiner* — Alexander S Noguerola
(74) *Attorney, Agent, or Firm* — Alston & Bird LLP

(57) ABSTRACT

An electrochemical $H_2S$ sensor comprises a housing, an electrolyte disposed within the housing, and a plurality of electrodes in contact with the electrolyte within the housing. The plurality of electrodes comprises a working electrode and a counter electrode. A surface area of the working electrode in contact with the electrolyte is less than a surface area of the counter electrode in contact with the electrolyte.

18 Claims, 2 Drawing Sheets

(56) References Cited

U.S. PATENT DOCUMENTS

| | | | |
|---|---|---|---|
| 2012/0125772 A1 | 5/2012 | Steeter et al. | |
| 2012/0148936 A1 | 6/2012 | Uensal et al. | |
| 2013/0153442 A1 | 6/2013 | Chen et al. | |
| 2014/0311905 A1 | 10/2014 | Stetter et al. | |
| 2018/0266983 A1 | 9/2018 | Yu et al. | |
| 2019/0025243 A1 | 1/2019 | Yu et al. | |

FOREIGN PATENT DOCUMENTS

| | | | | |
|---|---|---|---|---|
| CN | 101806765 A | | 8/2010 | |
| CN | 102239407 A | | 11/2011 | |
| CN | 102498239 A | | 6/2012 | |
| CN | 102621205 A | * | 8/2012 | ............. G01N 27/30 |
| CN | 102803947 A | | 11/2012 | |
| CN | 103018295 A | | 4/2013 | |
| CN | 103336041 A | | 10/2013 | |
| CN | 104880499 A | | 9/2015 | |
| CN | 108139373 A | | 6/2018 | |
| EP | 1688736 A1 | | 8/2008 | |
| EP | 2791663 A1 | | 10/2014 | |
| EP | 3341722 A1 | | 7/2018 | |
| EP | 3403081 A1 | | 11/2018 | |
| JP | 2006098269 A | | 4/2006 | |
| JP | 2014-137342 A | | 7/2014 | |
| WO | 2004/102150 A3 | | 5/2005 | |
| WO | 2011016855 A1 | | 2/2011 | |
| WO | 2013/090015 A1 | | 6/2013 | |
| WO | 2017034541 A1 | | 3/2017 | |
| WO | 2017123205 A1 | | 7/2017 | |

OTHER PUBLICATIONS

PCT Application No. PCT/US2015/046554, International Search Report, dated Dec. 11, 2015, 4 pages.
PCT Application No. PCT/US2015/046554, Written Opinion of the International Searching Authority, dated Dec. 11, 2015, 6 pages.
Yu C et al., "Electrochemical H2S sensor with H2SO4 pre-treated Nation membrane as solid polymer electrolyte", Sensors and Actuators B: Chemical: International Journal Devoted to Research and Development of Physical and Chemical Transducers, Elsevier S.A., CH, vol. 86, No. 2-3, Sep. 20, 2002, pp. 259-265.
Wang Y et al., "Solid polymer electrolyte-based hydrogen sulfide sensor", Sensors and Actuators B: Chemical: International Journal Devoted to Research and Development of Physical and Chemical Transducers, Elsevier S.A., CH, vol. 87, No. 1, Nov. 15, 2002, pp. 115-121.
R.G.A. Wills et al., "The Use of Fluorocarbon Surfactants to Improve the Manufacture of PEM Fuel Cell Electrodes", Fuel Cells, vol. 9, No. 2, Apr. 1, 2009, pp. 148-156.
PCT Application No. PCT/US2015/046554, International Preliminary Report on Patentability, dated Mar. 8, 2018, 8 pages.
Europe Patent Application No. 15757411.2, Communication pursuant to Rules 161(1) and 162 EPC, dated May 24, 2018, 2 pages.
PCT Application No. PCT/US2016/012961, International Search Report, dated Sep. 8, 2016, 3 pages.
PCT Application No. PCT/US2016/012961, Written Opinion of the International Searching Authority, dated Sep. 8, 2016, 5 pages.
PCT Application No. PCT/US2016/012961, International Preliminary Report on Patentability, dated Jul. 17, 2018, 6 pages.
Europe Patent Application No. 16701382.0, Communication pursuant to Rules 161(1) and 162 EPC, dated Oct. 12, 2018, 3 pages.
CN Office Action, including Search report, dated Apr. 20, 2020 for CN Application No. 201680083433.
English Translation of CN Office Action, including Search Report, dated Apr. 20, 2020 for CN Application No. 201680083433.
CN Office Action dated Jun. 1, 2020 for CN Application No. 201580084061.
English Translation of CN Office Action dated Jun. 1, 2020 for CN Application No. 201580084061.
Non-Final Rejection dated Jul. 30, 2020 for U.S. Appl. No. 15/754,254.
Final Rejection dated Nov. 5, 2020 for U.S. Appl. No. 15/754,254.

* cited by examiner

ELECTROCHEMICAL SENSOR

CROSS-REFERENCE TO RELATED APPLICATIONS

The present application is the National Stage of International Application. No. PCT/US2016/012961 filed on Jan. 12, 2016 and entitled "Electrochemical Sensor" which is incorporated herein by reference as if reproduced in its entirety.

STATEMENT REGARDING FEDERALLY SPONSORED RESEARCH OR DEVELOPMENT

Not applicable.

REFERENCE TO A MICROFICHE APPENDIX

Not applicable.

BACKGROUND

In monitoring for the presence of hydrogen sulfide ($H_2S$), other gases such as carbon monoxide (CO) can be present. The additional gases can react at a working electrode in a hydrogen sulfide sensor. For example, the working electrode can comprise a noble metal that can catalyze the reaction of both hydrogen sulfide and carbon monoxide. As a result, the presence of carbon monoxide may create a cross-sensitivity in the hydrogen sulfide sensor, resulting in the false impression that greater levels of hydrogen sulfide are present in the ambient gases than are actually present. Due to the danger presented by the presence of hydrogen sulfide, the threshold level for triggering an alarm can be relatively low, and the cross-sensitivity due to the presence of the carbon monoxide may be high enough to create a false alarm for the hydrogen sulfide sensor.

Some sensors are corrected for cross-sensitivity by calibrating the sensor in the presence of multiple gases including CO and $H_2S$. The readings for the $H_2S$ can be corrected to take into account the presence of the CO, which may result in an artificially low $H_2S$ reading in the absence of CO. This low reading may create a safety hazard when $H_2S$ is present in the gas being monitored.

SUMMARY

In an embodiment, an electrochemical $H_2S$ sensor comprises a housing, an electrolyte disposed within the housing, and a plurality of electrodes in contact with the electrolyte within the housing. The plurality of electrodes comprises a working electrode and a counter electrode. A surface area of the working electrode in contact with the electrolyte is less than a surface area of the counter electrode in contact with the electrolyte.

In an embodiment, an electrochemical $H_2S$ sensor comprises a housing, an electrolyte disposed within the housing, and a plurality of electrodes in contact with the electrolyte within the housing. The plurality of electrodes comprises a working electrode and a counter electrode. The working electrode comprises Pt—Ru and an additional catalytic material. The additional catalytic material comprises Ir, graphite, carbon, or any combination thereof, and the counter electrode comprises a perfluorosulfonic acid ion-exchange resin and Pt—Ru black.

In an embodiment, a method of detecting hydrogen sulfide comprises receiving an ambient gas into a housing of a hydrogen sulfide sensor, contacting the ambient gas with the porous working electrode, allowing the ambient gas to diffuse through the porous working electrode to contact an electrolyte, generating a current between the porous working electrode and the counter electrode in response to a reaction between the ambient gas and the electrolyte at the second surface of the working electrode, and determining a concentration of the hydrogen sulfide in the ambient gas based on the current. The ambient gas comprises hydrogen sulfide and carbon monoxide, and the hydrogen sulfide sensor comprises a plurality of electrodes in contact with an electrolyte within the housing. The plurality of electrodes comprises a porous working electrode and a counter electrode. The porous working electrode has a surface area in contact with the electrolyte that is less than a surface area of the counter electrode in contact with the electrolyte.

These and other features will be more clearly understood from the following detailed description taken in conjunction with the accompanying drawings and claims.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

DETAILED DESCRIPTION

Figure 1:
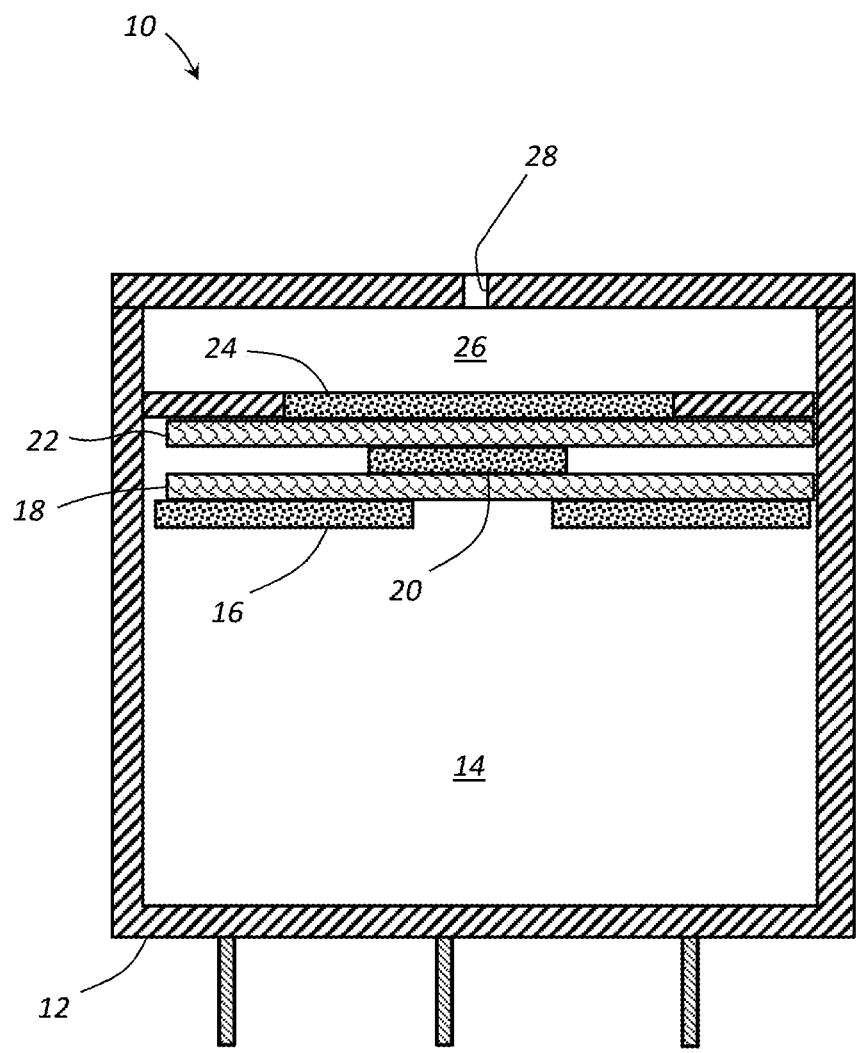
FIG. 1 schematically illustrates a cross section drawing of an electrochemical sensor according to an embodiment.

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

The following brief definition of terms shall apply throughout the application:

The term "comprising" means including but not limited to, and should be interpreted in the manner it is typically used in the patent context;

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as "exemplary" or an "example," it should be understood that refers to a non-exclusive example;

The terms "about" or "approximately" or the like, when used with a number, may mean that specific number, or alternatively, a range in proximity to the specific number, as understood by persons of skill in the art field; and If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

Due to the extreme toxicity of $H_2S$ gas, various countries have created regulations limiting the exposure of individuals to the gas. For example, the 2010 American Conference of Governmental Industrial Hygienists (ACGIH) has determined the $H_2S$ safety value at an 8 hour time weighted average (TWA-8 hr) of 1 ppm and a 15 minute short term exposure (STEL-15 min) of 5 ppm. Various sensors have been developed to detect the presence and concentration of $H_2S$ in the atmosphere. Electrochemical sensors using a noble metal catalyst to allow the $H_2S$ to react to create a measurable current may also catalyze the reaction of other gas species such as CO to create an electrical current. For example, an ambient concentration of 10 ppm CO can create a cross-sensitivity of around 5 ppb of $H_2S$ in a sensor having a low cross-sensitivity. However, the use of low cross-sensitivity sensors can experience slow response times, thereby making the sensors unfavorable in some situations.

Other sensors can have a faster response time, but may also have a higher cross-sensitivity to CO. For example, an ambient concentration of 50 ppm CO may create a cross-sensitivity reading of between about 0.5 to about 2.3 ppm $H_2S$. This reading may be sufficient to cause a false alarm for the 8 hour average and can create a false alarm for the short term exposure when higher concentrations of CO are present. Accordingly, the removal or reduction of cross-sensitivity to CO in an $H_2S$ sensor may improve safety.

There are a number of ways to enhance the selectivity of electrochemical sensors. First, the selection of the material for the working electrode can affect the overall sensitivity to various chemicals, including a relative sensitivity difference between the target gas and one or more interfering gases. Second, a filter can be used to remove the interfering gas, thereby reducing the cross-sensitivity to the interfering gases. However, the filter typically uses an absorbent or adsorbent that has a limited capacity, thereby limiting the effective life of the sensor. Third, an intermediary electrolyte system can be used. In this system, the selection of the composition of the electrolyte may be carried out so that the electrolyte selectively reacts with the target gases rather than the interfering gases. However, this method can be very complex, and the electrolyte can also have capacity restrictions leading to a limited useful life of the sensor. Fourth, the potential across the electrodes can be selected to remove or reduce the cross sensitivity of the sensor. Further, in some instances the cross sensitivity can be reduced by enlarging the capillary hole. However, this may result in a larger potential being developed in the sensor, which may affect a number of parameters in the sensor design, which may not be suitable for a sensor with a defined sensitivity.

As a novel manner of changing the cross-sensitivity of the electrochemical sensor, the electrochemical gas sensor can have a reduced working electrode surface area relative to the counter electrode surface area and/or a non-catalytically active or less catalytically active material with respect to the interfering gases can be added into the working electrode. The resulting sensor can have good response to $H_2S$ gas while at the same time having a reduced cross-sensitivity to CO gas.

In general, the electrochemical sensor disclosed herein comprises a gas diffusion working electrode, a counter electrode, and optionally, a reference electrode. Each electrode is in contact with an aqueous electrolyte. In order to reduce the potential cross-interference of any interfering gas or gases, the surface area of the working electrode can be reduced relative to the counter electrode such that the working electrode has a smaller surface area in contact with the electrolyte than the surface area of the counter electrode in contact with the electrolyte. This configuration can result in an electrochemical sensor having good sensitivity to $H_2S$ gas while at the same time having a reduced cross-sensitivity to CO.

In some embodiments, an additional catalyst material that is non-catalytically active or less catalytically active to the interfering gas or gases than the target gas can be used with the working electrode. This, can also reduce the cross sensitivity of CO gas.

The difference in the relative surface area of the working electrode to the counter electrode and/or the use of the different catalytically active material can be understood in terms of the relative control rates occurring within the sensor. While not intending to be limited by theory, the reaction rate for the target gas is mainly diffusion controlled when the catalytic activity is high enough. As a result, the catalyst effects on the overall reaction rate can be ignored. However, for the interfering gases, the electrochemical sensor is generally subject to both diffusion limitations and catalytic reaction rate limitations. As a result, the catalytic reaction rate limitations for the interfering gases affect the overall reaction rate. This concept is represented by the following equations.

For the target gas, $$\frac{1}{i_1} = \frac{1}{id_1} \qquad (Eq.\ 1)$$

where $id_1$ is the diffusion resistance of the sensor to the target gas with its diffusion capillary, and $i_1$ is the response current to the target gas with a concentration of C with the diffusion capillary. And for the interfering gas:

$$\frac{1}{i_2} = \frac{1}{id_2} + \frac{1}{i_{cat}} \qquad (Eq.\ 2)$$

where $id_2$ is the diffusion resistance of the sensor to the interfering gas with its diffusion capillary, $i_{cat}$ is the catalytic resistance to the interfering gases, and $i_2$ is the response current to the interfering gas with concentration of $C_2$ with the diffusion capillary.

As can be seen in the equations, the reduction in the surface area of the working electrode can have the same diffusion resistance to the interfering gases, but because the working electrode surface area is reduced, the catalytic current resulting from the reaction of the interfering gases $i_{cat}$ is reduced so that the overall response current to the interfering gases $i_2$ is reduced. Overall, the cross-sensitivity can be represented as:

$$\text{Cross sensitivity} = \frac{i_2}{\left(\frac{i_1}{C}\right)} \qquad (Eq.\ 3)$$

When $i_2$ is decreased, and $i_1$ and C remain unchanged, the cross-sensitivity can be reduced.

As disclosed herein, the surface area of the working electrode can be reduced to 20% to 70% of previous sensors in which the area of the working electrode and the counter electrode are approximately the same. As a result, the surface area of the working electrode can be reduced to an amount between about 20% and 70% of the original value. In general, the working electrode and the counter electrode can have approximately the same size. Thus, reducing the size of the working electrode can result in an electrochemical sensor having a surface area that is 20% to 70% less than the surface area of the counter electrode. In some embodiments, the use of a non-catalytically active catalyst or a catalytic material having a reduced activity with respect to the interfering gas or gases can also serve to reduce the cross-sensitivity of the sensor towards the interfering gas.

FIG. 1. is the cross section drawing of the electrochemical sensor 10. The sensor 10 generally comprises a housing 12 defining a cavity or reservoir 14 designed to hold an electrolyte solution. A working electrode 24 can be placed between an opening 28 and the reservoir 14. A counter electrode 16 and a reference electrode 20 can be positioned within the reservoir. When the gas reacts within the reservoir 14, an electrical current and/or potential can be developed between the electrodes to provide an indication of the concentration of the gas. A reference electrode 20 may also be positioned within the reservoir 14 to provide a reference for the detected current and potential between the working electrode 24 and the counter electrode 16.

The housing 12 defines the interior reservoir 14, and one or more openings 28 can be disposed in the housing to allow a gas to be detected to enter the housing 12 into a gas space 26. The housing 12 can generally be formed from any material that is substantially inert to the electrolyte and gas being measured. In an embodiment, the housing 12 can be formed from a polymeric material, a metal, or a ceramic. For example, the housing can be formed from a material including, but not limited to, acrylonitrile butadiene styrene (ABS), polyphenylene oxide (PPO), polystyrene (PS), polypropylene (PP), polyethylene (PE) (e.g., high density polyethylene (HDPE)), polyphenylene ether (PPE), or any combination or blend thereof.

One or more openings 28 can be formed through the housing 12 to allow the ambient gas to enter the gas space 26 and/or allow any gases generated within the housing to escape. In an embodiment, the electrochemical sensor 10 may comprise at least one inlet opening 28 to allow the ambient gas to enter the housing 12. The opening 28 can be disposed in a cap when a cap is present and/or in a wall of the housing 12. In some embodiments, the opening 28 can comprise a diffusion barrier to restrict the flow of gas (e.g., carbon monoxide, hydrogen sulfide, etc.) to the working electrode 24. The diffusion barrier can be created by forming the opening 28 as a capillary and/or a film or membrane can be used to control the mass flow rate through the one or more openings 28.

In an embodiment, the opening 28 may serve as a capillary opening to provide a rate limited exchange of the gases between the interior and exterior of the housing 12. In an embodiment, the opening 28 may have a diameter between about 200 µm and about 1.5 mm, where the opening 28 can be formed using a convention drill for larger openings and a laser drill for smaller openings. The opening 28 may have a length between about 0.5 mm and about 5 mm, depending on the thickness of the cap or housing 12. In some embodiments, two or more openings may be present for the inlet gases. When a membrane is used to control the gas flow into and/or out of the housing, the opening diameter may be larger than the sizes listed above as the film can contribute to and/or may be responsible for controlling the flow rate of the gases into and out of the housing 12.

The reservoir comprises the counter electrode 16, the reference electrode 20, and the working electrode 24. In some embodiment, the electrolyte can be contained within the reservoir 14, and the counter electrode 16, the reference electrode 20, and the working electrode 24 can be in electrical contact through the electrolyte. In some embodiments, one or more porous separators 18, 22 or other porous structures can be used to retain the electrolyte in contact with the electrodes. The separators 18, 22 can comprise a porous member that acts as a wick for the retention and transport of the electrolyte between the reservoir and the electrodes while being electrically insulating to prevent shorting due to direct contact between any two electrodes. One or more of the porous separator 18, 22 can extend into the reservoir to provide the electrolyte a path to the electrodes. In an embodiment, a separator 18 can be disposed between the counter electrode 16 and the reference electrode 20, and a separator 22 can be disposed between the reference electrode 20 and the working electrode 24.

One or more of the separators 18, 22 can comprise a nonwoven porous material (e.g., a porous felt member), a woven porous material, a porous polymer (e.g., an open cell foam, a solid porous plastic, etc.), or the like, and is generally chemically inert with respect to the electrolyte and the materials forming the electrodes. In an embodiment, the separator 18, 22 can be formed from various materials that are substantially chemically inert to the electrolyte including, but not limited to, glass (e.g., a glass mat), polymer (plastic discs), ceramics, or the like.

The electrolyte can be any conventional aqueous acidic electrolyte such as sulfuric acid, phosphoric acid, or a neutral ionic solution such as a salt solution (e.g., a lithium salt such as lithium chloride, etc.), or any combination thereof. For example, the electrolyte can comprise sulfuric acid having a molar concentration between about 3 M to about 12 M. Since sulfuric acid is hygroscopic, the concentration can vary from about 10 to about 70 wt % (1 to 11.5 molar) over a relative humidity (RH) range of the environment of about 3 to about 95%. In an embodiment, the electrolyte can comprise phosphoric acid having a concentration in an aqueous solution between about 30% to about 60% $H_3PO_4$ by weight. As another example, the electrolyte can include a lithium chloride salt having about 30% to about 60% LiC by weight, with the balance being an aqueous solution.

In some embodiments, the electrolyte may be in the form of a solid polymer electrolyte which comprises an ionic exchange membrane. In some embodiments, the electrolyte can be in the form of a free liquid, disposed in a matrix or slurry such as glass fibers (e.g., the separator 18, the separator 22, etc.), or disposed in the form of a semi-solid or solid gel.

The working electrode 24 may be disposed within the housing 12. The gas entering the sensor 10 can contact one side of the working electrode 24 and pass through working electrode 24 to reach the interface between the working electrode 24 and the electrolyte. The gas can then react to generate the current indicative of the gas concentration. As disclosed herein, the working electrode 24 can comprise a plurality of layers. The base or substrate layer can comprise a hydrophobic material or a hydrophobically treated material. A catalytic material can be formed as an electrode on one side of the working electrode 24 and placed in contact with the electrolyte.

In an embodiment, the working electrode 24 can comprise a porous substrate or membrane as the base layer. The substrate can be porous to the gas of interest, which can comprise hydrogen sulfide. In an embodiment, the substrate can comprise a carbon paper formed of carbon or graphite fibers. In some embodiments, the substrate can be made to be electrically conductive through the addition of a conductive material such as carbon. The use of carbon may provide a sufficient degree of electrical conductivity to allow the current generated by the reaction of the gas with the electrolyte at the surface of the working electrode 24 to be detected by a lead coupled to the working electrode 24. Other electrically conductive substrates may also be used such as carbon felts, porous carbon boards, and/or electrically conductive polymers such as polyacetylene, each of which may be made hydrophobic as described below. Alternatively, an electrically conductive lead can be coupled to the catalytic layer to electrically couple the catalytic material to the external circuitry, as described in more detail herein. In an embodiment, the substrate can be between about 5 mils to about 20 mils thick in some embodiments.

The porous substrate can be hydrophobic to prevent the electrolyte from passing through the working electrode 24. The substrate can be formed from a hydrophobic material, or the substrate can be treated with a hydrophobic material. In an embodiment, the substrate can be made hydrophobic through the impregnation of the substrate with a hydrophobic material such as a fluorinated polymer (e.g., PTFE, etc.). In some embodiments, the substrate or membrane can comprise GEFC-IES (e.g., the copolymer of perfluorosulfonic acid and PTFE, which is commercially available from Golden Energy Fuel Cell Co., Ltd.), Nafion® (a copolymer of polytetrafluoroethylene and perfluoro-3,6-dioxa-4-methyl-7-octene-sulfonic acid, which is commercially available from Dupont™), or pure or nearly pure polytetrafluoroethylene (PTFE). The impregnation process can include disposing a hydrophobic material containing solution or slurry on the substrate using a dipping, coating, or rolling process. Alternatively, a dry composition such as a powder can be applied to the substrate. In some embodiments, an optional sintering process can be used to infuse the hydrophobic material into the substrate to create the hydrophobic base layer for the working electrode 24, where both sides of the hydrophobic base layer are hydrophobic. The sintering process can cause the hydrophobic polymer to bond or fuse with the carbon of the substrate to securely bond the hydrophobic material to the substrate.

The resulting substrates can contain about 30% to about 50% by weight of the hydrophobic polymer. The amount of hydrophobic material added to the substrate can affect the electrical conductivity of the substrate, wherein the electrical conductivity tends to decrease with an increased amount of the hydrophobic material. The amount of the hydrophobic polymer used with the substrate may depend on the degree of hydrophobicity desired, the porosity to the hydrogen sulfide, and the resulting electrical conductivity of the working electrode.

The catalytic layer can be formed by mixing the desired catalyst with a binder and depositing the mixture on the substrate material. The binder can comprise a solution of perfluorinated ion electrolyte solution (e.g., GEFC-IES, Nafion®, etc.), a hydrophobic material such as PTFE, mixtures thereof, or the like. When used as a binder, the GEFC-IES Nafion®, and/or PTFE can affect the gas diffusion parameters while supporting the electrocatalyst and maximizing the interfaces between catalyst, gas and electrolyte at which the electrochemical processes occur. Glycol or other similar chemicals can be used as a diluent to form a catalyst slurry, recipe or catalyst system, which can be printed on a substrate by a printer.

The catalytic layer might be deposited onto the substrate by for example screen printing, filtering in selected areas from a suspension placed onto the substrate, by spray coating, or any other method suitable for producing a patterned deposition of solid material. Deposition might be of a single material or of more than one material sequentially in layers, so as for example to vary the properties of the electrode material through its thickness or to add a second layer of increased electrical conductivity above or below the layer which is the main site of gas reaction. Once deposited, the printed element can be sintered at an elevated temperature to form the electrode.

In the working electrode 24, the catalytic layer can comprise carbon (e.g., graphite) and/or one or more metals or metal oxides such as copper, silver, gold, nickel, palladium, platinum, ruthenium, iridium, and/or oxides of these metals. The catalyst used can be a pure metal powder, a metal powder combined with carbon, or a metal powder supported on an electrically conductive medium such as carbon, or a combination of two or more metal powders either as a blend or as an alloy. The materials used for the individual electrodes can be the same or different. In an embodiment, the working electrode 24 comprises a platinum-ruthenium black (Pt—Ru black) electrode. The atomic ratio of the Pt to Ru in the Pt—Ru black can be in the range of about 1:1 to about 1:5, or about 1:2. The catalyst material can have a weight loading per square centimeter ($cm^2$) of the surface area of the working electrode 24 of between about 0.1 $mg/cm^2$ and about 5 $mg/cm^2$, or between about 0.5 $mg/cm^2$ and about 2 $mg/cm^2$, or about 1 $mg/cm^2$.

The counter electrode 16 can be disposed within the housing 12. The counter electrode 16 can comprise a substrate or membrane such as a PTFE membrane, a GEFC-IES membrane, a Nafion® membrane, or the like having a catalytic material disposed thereon. In an embodiment, the catalytic material can be mixed and disposed on the membrane using any suitable process such as rolling, coating, screen printing, or the like to apply the catalytic material on the membrane, as described in more detail herein. The catalyst layer can then be bonded to the membrane through a sintering process as described herein.

In an embodiment, the catalytic material for the counter electrode can comprise a noble metal such as gold (Au), platinum (Pt), ruthenium (Ru), rhodium (Rh), Iridium (Ir), oxides thereof, or any combination thereof. In an embodiment, the catalytic material comprises a Pt—Ru mixture that is screen printed on the membrane, where the membrane can be a GEFC-IES membrane. The catalyst loading for the counter electrode 16 can be within any of the ranges described herein for the working electrode 24. In an embodiment, the catalyst loading for the counter electrode 16 can be the same or substantially the same as the catalyst loading for the working electrode 24, the catalyst loading can also be greater than or less than that of the working electrode 24.

When the electrochemical sensor 10 is used to detect hydrogen sulfide, the relative size or surface area of the working electrode 24 can be reduced relative to the size or surface area of the counter electrode 16. By reducing the size of the working electrode, the cross-sensitivity to CO can be reduced to acceptable levels. In an embodiment, a surface area of the working electrode 24 in contact with the electrolyte may be between about 30% to about 80%, or between about 45% to about 70% of the surface area of the counter electrode. In some embodiments, the working electrode can be circular and have a diameter between about 2 mm and about 6 mm, or between about 2.5 mm and about 5 mm. The counter electrode can similarly be circular and have a diameter between about 6.5 mm and about 8 mm, or about 7 mm.

In some embodiments, the catalyst loading for the working electrode 24 and the counter electrode 16 can be approximately the same in terms of weight per unit of surface area. Since the working electrode 24 can have a lower surface area than the counter electrode 16, the absolute amount of catalyst present in the working electrode 24 can be less than the amount of catalyst in the counter electrode 16.

In an embodiment, a catalytic material can be added to the working electrode 24 that has a higher catalytic activity towards the target gas such as hydrogen sulfide than an interfering gas or gases such as carbon monoxide. When the target gas is hydrogen sulfide and the interfering gas is carbon monoxide, the catalytic material that can be added into the working electrode can comprise graphite, carbon (e.g., carbon black), iridium, or any combination thereof. A weight ratio of the additional catalytic material to the amount of catalyst (e.g., Pt—Ru black) in the working electrode can be in the range of about 1:1 to about 1:2. The use of the additional catalytic material can occur in combination with a reduced size of the working electrode 24 relative to the counter electrode 16 or when the working electrode 24 and the counter electrode 16 have approximately the same size.

Similarly, the reference electrode 20 can be disposed within the housing 12. The reference electrode 20 can comprise a substrate or membrane such as a PTFE membrane, a GEFC-IES membrane, a Nafion® membrane, or the like having a catalytic material disposed thereon. In an embodiment, the catalytic material can be mixed with a hydrophobic material (e.g., PTFE, etc.) and disposed on the PTFE membrane. Any of the methods used to form the working electrode or the counter electrode can also be used to prepare the reference electrode 20. In an embodiment, the catalytic material used with the reference electrode 20 can comprise a noble metal such as gold (Au), platinum (Pt), ruthenium (Ru), rhodium (Rh), Iridium (Ir), oxides thereof, or any combination thereof. In an embodiment, the catalytic material used to form the reference electrode can comprise a Pt—Ru mixture that is screen printed on the membrane, where the membrane can be a GEFC-IES membrane. The catalyst loading for the reference electrode 20 can be within any of the ranges described herein for the working electrode 24. In an embodiment, the catalyst loading for the reference electrode 20 can be the same or substantially the same as the catalyst loading for the working electrode 24, the catalyst loading can also be greater than or less than that of the working electrode 24. While illustrated in FIG. 1 as having the reference electrode 20, some embodiments of the electrochemical sensor may not include a reference electrode 20.

In order to detect the current and/or potential difference across the electrodes in response to the presence of the hydrogen sulfide, one or more leads or electrical contacts can be electrically coupled to the working electrode 24, the reference electrode 20, and/or the counter electrode 16. The lead contacting the working electrode 24 can contact either side of the working electrode 24 since the substrate comprises an electrically conductive material. In order to avoid the corrosive effects of the electrolyte, the lead contacting the working electrode can contact the side of the working electrode 24 that is not in contact with the electrolyte. Leads may be similarly electrically coupled to the counter electrode 16 and the reference electrode 20. The leads can be electrically coupled to external connection pins to provide an electrical connection to external processing circuitry. The external circuitry can detect the current and/or potential difference between the electrodes and convert the current into a corresponding hydrogen sulfide concentration.

In use, the sensor 10 can detect a hydrogen sulfide concentration in the presence of carbon monoxide. In use, the ambient gas can flow into the sensor 10 through the opening 28, which serves as the intake port for the sensor 10. The ambient gas can comprise hydrogen sulfide and/or carbon monoxide. The gas can contact the working electrode and pass through the fine pores of the porous substrate layer to reach the surface of the working electrode 24 treated with the catalyst layer. The electrolyte may be in contact with the surface of the working electrode 24, and the hydrogen sulfide may react and result in an electrolytic current forming between the working electrode 24 and the counter electrode 16 that corresponds to the concentration of the hydrogen sulfide in the ambient gas. By measuring the current, the concentration of hydrogen sulfide can be determined using, for example, the external detection circuitry.

During the measurement process, an interfering gas such as the carbon monoxide can also contact the working electrode 24. The carbon monoxide can react at the surface of the working electrode 24, though the carbon monoxide may not react at the same rate. The carbon monoxide may also experience a diffusional resistance within the sensor 10. In an embodiment, the surface area of the working electrode 24 may be less than the surface area of the counter electrode 16 in contact with the electrolyte. As a result, the current generated by the reaction of the carbon monoxide at the working electrode 24 can be reduced relative to the current generated by the reaction of the hydrogen sulfide at the working electrode 24. The relative contribution of the carbon monoxide to the current may then be reduced to an acceptable level.

In an embodiment in which an additional catalytic material is added to the working electrode 24, the reaction rate of the hydrogen sulfide at the working electrode 24 can be significantly faster than the reaction of carbon monoxide at the working electrode 24. By adding the catalytic material having a higher reactivity for hydrogen sulfide than for carbon monoxide, the relative contribution to the overall current from the reaction of the hydrogen sulfide can be significantly greater than the contribution from the reaction of carbon monoxide, which may reduce the cross-sensitivity of the sensor 10 to carbon monoxide to an acceptable level.

When the working electrode 24 surface area is reduced relative to the surface area of the counter electrode 16, when an additional catalytic material is added to the working electrode 24, or any combination thereof, the cross-sensitivity of the sensor 10 may be less than a comparable sensor without these features. In an embodiment a ratio of: 1) the sensitivity (e.g., as expressed as current per concentration unit such as in units of A/ppm, or the like) of the electrochemical sensor to hydrogen sulfide to 2) the sensitivity (e.g., in units of MA/ppm, etc.) or cross-sensitivity of the electrochemical sensor to carbon monoxide can be greater than about 20, greater than about 40, greater than about 50, greater than about 60, greater than about 80, greater than about 100, or greater than about 125 using the sensor 10 as described herein. In an embodiment, the ratio of: 1) the sensitivity of the electrochemical sensor to hydrogen sulfide to the sensitivity of the electrochemical sensor to carbon monoxide can be generally less than about 300, or less than about 200, and the ratio can be in any range from any of the lower end points to any of the upper end points.

EXAMPLES

The disclosure having been generally described, the following examples are given as particular embodiments of the disclosure and to demonstrate the practice and advantages thereof. It is understood that the examples are given by way of illustration and are not intended to limit the specification or the claims in any manner.

Example 1

Figure 2:
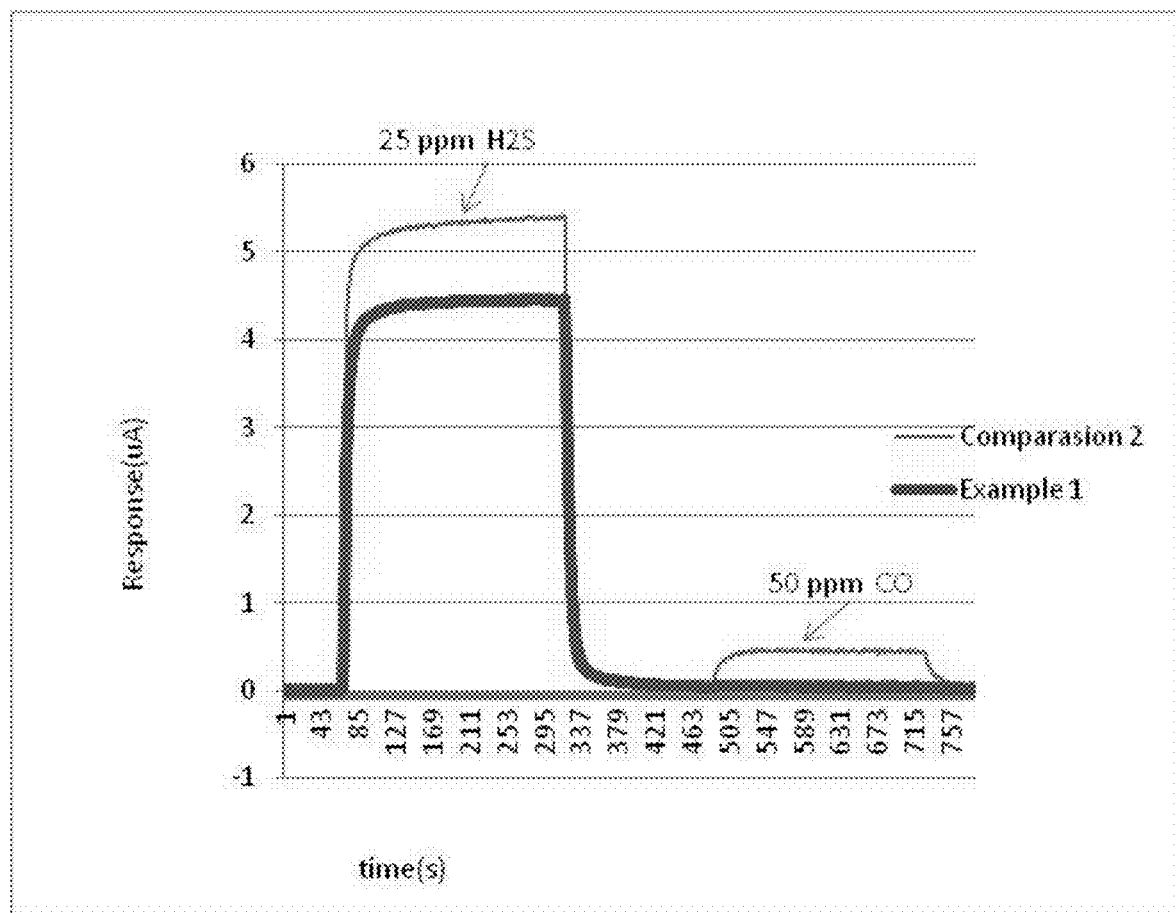
FIG. 2 illustrates a sensor response to exposure to 25 ppm $H_2S$ followed by 50 ppm of CO under the conditions described in Examples 1 and 3.

An electrochemical sensor was prepared with a reduced area working electrode relative to the counter electrode. In this example, an electrochemical $H_2S$ sensor was prepared with a capillary hole having a 1 mm diameter. The working electrode, the reference electrode, and the counter electrode were prepared from GEFC and Pt:Ru, where the atomic ratio of Pt to Ru was 1:2. The catalyst loading was 1 mg/cm$^2$, the working electrode diameter is 4.5 mm. The sensor was first tested with 25 ppm $H_2S$, and the resulting sensitivity was 0.18 uA/ppm with a T90 of 15 seconds, a baseline of 0.04 uA, and a resolution 0.1 ppm. This is shown in FIG. 2 by the bold line. The sensor was then exposed to air for 3 min, and then 50 ppm of CO for 4 min. The resulting CO cross sensitivity to $H_2S$ was 0.2 ppm equivalent, as can be seen in FIG. 2 in the bold line.

Example 2

An electrochemical sensor was prepared with an additional catalytic material in the working electrode. In this example, an electrochemical $H_2S$ sensor was prepared with a capillary hole with 1 mm diameter. The working electrode was made by GEFC and Pt—Ru black and Ir black, where the weight ratio of Pt—Ru to Ir was 1:1. The reference electrode and the counter electrode were prepared with GEFC and Pt:Ru and the atomic ratio of Pt to Ru was 1:2. The catalyst loading was 1 mg/cm$^2$, and the working electrode diameter was 7 mm. The sensor was tested with 25 ppm $H_2S$, and the resulting sensitivity was 0.19 uA/ppm with a T90 of 10 s, a baseline of 0.01 uA, and a resolution 0.1 ppm. The sensor was then exposed to 3 min air, followed by 50 ppm CO for 4 min. The CO cross sensitivity to $H_2S$ was 0.3 ppm equivalent.

Example 3

A comparison example was conducted to demonstrate the benefits of the configurations disclosed herein. In this example, an electrochemical $H_2S$ sensor was prepared with a capillary hole having a 1 mm diameter. The working electrode was made with GEFC and Pt—Ru black. The reference electrode and the counter electrode were prepared with GEFC and Pt:Ru, where the atomic ratio of Pt to Ru was 1:2. The catalyst loading was 1 mg/cm2, and the working electrode diameter was 7 mm. The sensor was tested with 25 ppm $H_2S$, the resulting sensitivity was 0.21 uA/ppm with a T90 of 10 s, a baseline of 0.00 uA, and a resolution 0.1 ppm. The sensor was then exposed to air for 3 min followed by 50 ppm CO. The CO cross sensitivity to $H_2S$ was 2.1 ppm equivalent as can be seen of the thin line in the FIG. 2.

Having disclosed various embodiments and methods herein, several embodiments can include, but are not limited to:

In a first embodiment, an electrochemical $H_2S$ sensor (10) comprises a housing (12), an electrolyte disposed within the housing (12), and a plurality of electrodes (24, 16) in contact with the electrolyte within the housing (12), wherein the plurality of electrodes (24, 16) comprises a working electrode (24) and a counter electrode (16), wherein a surface area of the working electrode (24) in contact with the electrolyte is less than a surface area of the counter electrode (16) in contact with the electrolyte.

A second embodiment can include the sensor of the first embodiment, wherein the surface area of the working electrode (24) in contact with the electrolyte is between 20% and 75% of the surface area of the counter electrode (16) in contact with the electrolyte.

A third embodiment can include the sensor of the first or second embodiment, wherein the working electrode (24) comprises a perfluorosulfonic acid ion-exchange resin and Pt—Ru disposed on a perfluorosulfonic acid ion-exchange resin membrane.

A fourth embodiment can include the sensor of the third embodiment, wherein the working electrode comprises a catalytic material having no catalytic reactivity or a lower catalytic reactivity with respect to an interference gas than to a target gas than Pt or Ru.

A fifth embodiment can include the sensor of the fourth embodiment, wherein the interference gas is carbon monoxide, and wherein the target gas is hydrogen sulfide.

A sixth embodiment can include the sensor of the fourth or fifth embodiment, wherein the catalytic material comprises Ir, graphite, carbon, or any combination thereof.

A seventh embodiment can include the sensor of any of the fourth to sixth embodiments, wherein a weight ratio of the catalytic material to the Pt—Ru is in a range of from 1:1 to 1:2.

An eighth embodiment can include the sensor of any of the fourth to seventh embodiments, wherein the counter electrode (16) comprises a perfluorosulfonic acid ion-exchange resin and Pt—Ru disposed on a perfluorosulfonic acid ion-exchange resin membrane.

A ninth embodiment can include the sensor of any of the fourth to eighth embodiments, wherein the plurality of electrodes further comprises a reference electrode (20), and wherein the reference electrode (20) comprises a perfluorosulfonic acid ion-exchange resin and Pt—Ru disposed on a perfluorosulfonic acid ion-exchange resin membrane.

A tenth embodiment can include the sensor of any of the fourth to ninth embodiments, wherein the electrolyte comprises H2SO4, H3PO4, or any combination thereof.

In an eleventh embodiment, an electrochemical H2S sensor (10) comprises a housing (12), an electrolyte disposed within the housing (12), and a plurality of electrodes (24, 16) in contact with the electrolyte within the housing (12), wherein the plurality of electrodes (24, 16) comprise: a working electrode (24), wherein the working electrode (24) comprises Pt—Ru, and an additional catalytic material, wherein the additional catalytic material comprises Ir, graphite, carbon, or any combination thereof; and a counter electrode (16), wherein the counter electrode (16) comprises a perfluorosulfonic acid ion-exchange resin and Pt—Ru black.

A twelfth embodiment can include the sensor of the eleventh embodiment, wherein a weight ratio of the additional catalytic material to the Pt—Ru is in a range of from 1:1 to 1:2.

A thirteenth embodiment can include the sensor of the eleventh or twelfth embodiment, wherein an atomic ratio of the Pt—Ru in at least one of the working electrode or the counter electrode is in a range of from 1:1 to 1:4.

A fourteenth embodiment can include the sensor of any of the eleventh to thirteenth embodiments, wherein a surface area of the working electrode (24) in contact with the electrolyte is less than a surface area of the counter electrode (16) in contact with the electrolyte.

A fifteenth embodiment can include the sensor of any of the eleventh to fourteenth embodiments, wherein the sensor is configured to detect hydrogen sulfide, and wherein a ratio of 1) a sensitivity of the sensor to hydrogen sulfide to 2) a sensitivity of the sensor to carbon monoxide is greater than about 20.

In a sixteenth embodiment, a method of detecting hydrogen sulfide comprises receiving an ambient gas into a housing (12) of a hydrogen sulfide sensor, wherein the ambient gas comprises hydrogen sulfide and carbon monoxide, and wherein the hydrogen sulfide sensor comprises a plurality of electrodes (24, 16) in contact with an electrolyte within the housing (12), wherein the plurality of electrodes (24, 16) comprise a porous working electrode (24) and a counter electrode (16), contacting the ambient gas with the porous working electrode (24), wherein the porous wherein a surface area of the working electrode (24) in contact with the electrolyte is less than a surface area of the counter electrode (16) in contact with the electrolyte, allowing the ambient gas to diffuse through the porous working electrode (24) to contact an electrolyte, generating a current between the porous working electrode (24) and the counter electrode (16) in response to a reaction between the ambient gas and the electrolyte at the second surface of the working electrode (24), and determining a concentration of the hydrogen sulfide in the ambient gas based on the current.

A seventeenth embodiment can include the method of the sixteenth embodiment, wherein a ratio of 1) a sensitivity of the sensor to hydrogen sulfide to 2) a sensitivity of the sensor to carbon monoxide is greater than about 20, or alternatively, greater than about 50.

An eighteenth embodiment can include the method of the sixteenth or seventeenth embodiment, wherein the surface area of the working electrode (24) in contact with the electrolyte is between 20% and 75% of the surface area of the counter electrode (16) in contact with the electrolyte.

A nineteenth embodiment can include the method of any of the sixteenth to eighteenth embodiments, wherein the working electrode (24) comprises Pt—Ru, and an additional catalytic material, wherein the additional catalytic material comprises Ir, graphite, carbon, or any combination thereof, and wherein the counter electrode (16) comprises a perfluorosulfonic acid ion-exchange resin and Pt—Ru black.

A twentieth embodiment can include the method of the nineteenth embodiment, wherein a weight ratio of the additional catalytic material to the Pt—Ru is in a range of from 1:1 to 1:2.

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above, but is defined by the claims which follow, that scope including all equivalents of the subject matter of the claims. Each and every claim is incorporated as further disclosure into the specification and the claims are embodiment(s) of the present invention(s). Furthermore, any advantages and features described above may relate to specific embodiments, but shall not limit the application of such issued claims to processes and structures accomplishing any or all of the above advantages or having any or all of the above features.

Additionally, the section headings used herein are provided for consistency with the suggestions under 37 C.F.R. 1.77 or to otherwise provide organizational cues. These headings shall not limit or characterize the invention(s) set out in any claims that may issue from this disclosure. Specifically and by way of example, although the headings might refer to a "Field," the claims should not be limited by the language chosen under this heading to describe the so-called field. Further, a description of a technology in the "Background" is not to be construed as an admission that certain technology is prior art to any invention(s) in this disclosure. Neither is the "Summary" to be considered as a limiting characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of the claims shall be considered on their own merits in light of this disclosure, but should not be constrained by the headings set forth herein.

Use of broader terms such as "comprises", "includes", and "having" should be understood to provide support for narrower terms such as "consisting of", "consisting essentially of", and "comprised substantially of". Use of the term "optionally," "may," "might," "possibly," and the like with respect to any element of an embodiment means that the element is not required, or alternatively, the element is required, both alternatives being within the scope of the embodiment(s). Also, references to examples are merely provided for illustrative purposes, and are not intended to be exclusive.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. An electrochemical $H_2S$ sensor comprising:
a housing;
an electrolyte disposed within the housing; and
a plurality of electrodes in contact with the electrolyte within the housing,
wherein:
the plurality of electrodes comprise a working electrode and a counter electrode, wherein the counter electrode comprises a perfluorosulfonic acid ion-exchange resin and Pt—Ru disposed on a perfluorosulfonic acid ion-exchange resin membrane,
a surface area of the working electrode in contact with the electrolyte is less than a surface area of the counter electrode in contact with the electrolyte, and
the working electrode is configured to detect hydrogen sulfide due to the surface area of the working electrode in contact with the electrolyte being between 20% and 75% of the surface area of the counter electrode in contact with the electrolyte.

2. The sensor of claim 1, wherein the working electrode comprising a surface area in contact with the electrolyte between 20% and 75% of the surface area of the counter electrode in contact with the electrolyte results in a ratio of 1) a sensitivity of the sensor to hydrogen sulfide to 2) a sensitivity of the sensor to carbon monoxide greater than about 20.

3. The sensor of claim 1, wherein the working electrode comprises a perfluorosulfonic acid ion-exchange resin and Pt—Ru disposed on a perfluorosulfonic acid ion-exchange resin membrane.

4. The sensor of claim 3, wherein the working electrode comprises a catalytic material having a lower to no catalytic reactivity, with respect to carbon monoxide, than Pt or Ru.

5. The sensor of claim 4, wherein the catalytic material comprises Ir, graphite, carbon, or any combination thereof.

6. The sensor of claim 4, wherein a weight ratio of the catalytic material to the Pt—Ru is in a range of from 1:1 to 1:2.

7. The sensor of claim 1, wherein the electrolyte comprises $H_2S_{O4}$, $H_3PO_4$, or any combination thereof.

8. The sensor of claim 1, wherein the plurality of electrodes further comprises a reference electrode, and wherein the reference electrode comprises a perfluorosulfonic acid ion-exchange resin and Pt—Ru disposed on a perfluorosulfonic acid ion-exchange resin membrane.

9. An electrochemical $H_2S$ sensor comprising:
a housing;
an electrolyte disposed within the housing; and
a plurality of electrodes in contact with the electrolyte within the housing, wherein the plurality of electrodes comprise:
a working electrode, wherein the working electrode comprises Pt—Ru, and an additional catalytic material, wherein the additional catalytic material comprises Ir, graphite, carbon, or any combination thereof; and
a counter electrode, wherein the counter electrode comprises a perfluorosulfonic acid ion-exchange resin and Pt—Ru black.

10. The sensor of claim 9, wherein a weight ratio of the additional catalytic material to the Pt—Ru is in a range of from 1:1 to 1:2.

11. The sensor of claim 10, wherein the working electrode comprises a surface area in contact with the electrolyte between 20% and 75% of a surface area of the counter electrode in contact with the electrolyte, thereby resulting in a ratio of 1) a sensitivity of the sensor to hydrogen sulfide to 2) a sensitivity of the sensor to carbon monoxide greater than about 20.

12. The sensor of claim 9, wherein a ratio of the Pt—Ru and the additional catalytic material in at least one of the working electrode or the counter electrode is in a range of from 1:1 to 1:4.

13. The sensor of claim 9, wherein a surface area of the working electrode in contact with the electrolyte is less than a surface area of the counter electrode in contact with the electrolyte.

14. The sensor of claim 13, wherein the surface area of the working electrode results in a reduction in cross-sensitivity of the sensor to carbon monoxide of approximately 90% in comparison with sensitivity of the sensor for the detection of hydrogen sulfide.

15. A method of detecting hydrogen sulfide, the method comprising:
receiving an ambient gas into a housing of a hydrogen sulfide sensor, wherein the ambient gas comprises hydrogen sulfide and carbon monoxide, and wherein the hydrogen sulfide sensor comprises a plurality of electrodes in contact with an electrolyte within the housing, wherein the plurality of electrodes comprise a porous working electrode and a counter electrode, wherein the porous working electrode is configured to detect hydrogen sulfide while minimizing cross-sensitivity to carbon monoxide due to a surface area of the porous working electrode in contact with the electrolyte being between 20% and 75% of a surface area of the counter electrode in contact with the electrolyte;
contacting the ambient gas with the porous working electrode, wherein the surface area of the porous working electrode in contact with the electrolyte is less than the surface area of the counter electrode in contact with the electrolyte;
allowing the ambient gas to diffuse through the porous working electrode to contact the electrolyte;
generating a current between the porous working electrode and the counter electrode in response to a reaction between the ambient gas and the electrolyte at a second surface of the porous working electrode; and
determining a concentration of the hydrogen sulfide in the ambient gas based on the current, wherein the working electrode comprises Pt—Ru, and an additional catalytic material, and wherein the additional catalytic material comprises Ir, graphite, carbon, or any combination thereof, and wherein the counter electrode comprises a perfluorosulfonic acid ion-exchange resin and Pt—Ru black.

16. The method of claim 15, wherein the porous working electrode comprises the surface area in contact with the electrolyte between 20% and 75% of the surface area of the counter electrode in contact with the electrolyte, thereby resulting in a ratio of 1) a sensitivity of the sensor to hydrogen sulfide to 2) a sensitivity of the sensor to carbon monoxide greater than about 20.

17. The method of claim 15, wherein the surface area of the porous working electrode results in a reduction in cross-sensitivity of the sensor to carbon monoxide of approximately 90%.

18. The method of claim 15, wherein a weight ratio of the additional catalytic material to the Pt—Ru is in a range of 1:1 to 1:2.

* * * * *